(12) United States Patent
Pavlovic

(10) Patent No.: US 8,894,914 B2
(45) Date of Patent: Nov. 25, 2014

(54) METHOD FOR THE MANUFACTURE OF A CERMET-CONTAINING BUSHING

(75) Inventor: Goran Pavlovic, Schaafheim (DE)

(73) Assignee: Heraeus Precious Metals GmbH & Co., Hanau (DE)

( * ) Notice: Subject to any disclaimer, the term of this patent is extended or adjusted under 35 U.S.C. 154(b) by 314 days.

(21) Appl. No.: 13/361,398

(22) Filed: Jan. 30, 2012

(65) Prior Publication Data

US 2012/0200011 A1 Aug. 9, 2012

Related U.S. Application Data

(60) Provisional application No. 61/438,057, filed on Jan. 31, 2011.

(30) Foreign Application Priority Data

Jan. 31, 2011 (DE) .................. 10 2011 009 861

(51) Int. Cl.
*C04B 111/94* (2006.01)
*C22C 29/16* (2006.01)
(Continued)

(52) U.S. Cl.
CPC .............. *A61N 1/3754* (2013.01); *C22C 29/16* (2013.01); *C04B 35/6455* (2013.01);
(Continued)

(58) Field of Classification Search
CPC .................. C04B 2111/90; C04B 2111/905; C04B 2111/92; C04B 2111/94; C04B 2237/68
See application file for complete search history.

(56) References Cited

U.S. PATENT DOCUMENTS 3,979,187 A 9/1976 Scherer
4,152,540 A 5/1979 Duncan et al.
(Continued)

FOREIGN PATENT DOCUMENTS

DE 69729719 7/2005
DE 102006054249 5/2008
(Continued)

OTHER PUBLICATIONS

The Restriction Requirement for U.S. Appl. No. 13/361,322 mailed Nov. 14, 2013 (7 pages).
(Continued)

*Primary Examiner* — Joseph S Del Sole
*Assistant Examiner* — Russell Kemmerle, III
(74) *Attorney, Agent, or Firm* — Dicke, Billig & Czaja, PLLC

(57) ABSTRACT

One aspect relates to a method for the manufacture of an electrical bushing for use in a housing of an active implantable medical device. The electrical bushing includes an electrically insulating base body and an electrical conducting element. The conducting element is set-up to establish, through the base body, an electrically conducting connection between an internal space of the housing and an external space. The conducting element is hermetically sealed with respect to the base body. The conducting element includes at least one cermet.

One aspect provides the method including forming a base body green compact having a through-opening that extends through the base body green compact from a ceramic slurry, generating at least one conducting element green compact from a cermet slurry, producing a bushing blank by combining the conducting element green compact and the base body green compact, and separating the bushing blank into two electrical bushings.

9 Claims, 10 Drawing Sheets

(51) Int. Cl.
*C04B 35/645* (2006.01)
*C04B 35/119* (2006.01)
*A61N 1/375* (2006.01)
*C22C 29/12* (2006.01)

(52) U.S. Cl.
CPC ....... C04B 2235/3244 (2013.01); *C04B 35/645* (2013.01); *C04B 2235/5445* (2013.01); *C04B 2235/3217* (2013.01); *C04B 2235/6022* (2013.01); *C04B 2235/604* (2013.01); *C04B 2235/6021* (2013.01); *C04B 35/119* (2013.01); *C22C 29/12* (2013.01)
USPC ....................................................... 264/614

(56) References Cited

U.S. PATENT DOCUMENTS

| | | | |
|---|---|---|---|
| 4,217,137 | A | 8/1980 | Kraska et al. |
| 4,315,054 | A | 2/1982 | Sack et al. |
| 4,354,964 | A | 10/1982 | Hing et al. |
| 4,488,673 | A | 12/1984 | Hopper, Jr. |
| 4,678,868 | A | 7/1987 | Kraska et al. |
| 4,991,582 | A | 2/1991 | Byers et al. |
| 5,043,535 | A | 8/1991 | Lin |
| 5,515,604 | A * | 5/1996 | Horine et al. .................. 29/830 |
| 5,769,874 | A | 6/1998 | Dahlberg |
| 5,861,714 | A * | 1/1999 | Wei et al. ..................... 313/625 |
| 5,870,272 | A | 2/1999 | Seifried et al. |
| 6,093,476 | A * | 7/2000 | Horiuchi et al. .............. 428/209 |
| 6,414,835 | B1 | 7/2002 | Wolf et al. |
| 6,643,903 | B2 | 11/2003 | Stevenson et al. |
| 6,660,116 | B2 | 12/2003 | Wolf et al. |
| 6,999,818 | B2 | 2/2006 | Stevenson et al. |
| 7,035,076 | B1 | 4/2006 | Stevenson |
| 7,038,900 | B2 | 5/2006 | Stevenson et al. |
| 7,136,273 | B2 | 11/2006 | Stevenson et al. |
| 7,145,076 | B2 | 12/2006 | Knappen et al. |
| 7,174,219 | B2 | 2/2007 | Wahlstrand et al. |
| 7,260,434 | B1 | 8/2007 | Lim et al. |
| 7,274,963 | B2 | 9/2007 | Spadgenske |
| 7,437,817 | B2 | 10/2008 | Zhang et al. |
| 7,480,988 | B2 * | 1/2009 | Ok et al. ......................... 29/837 |
| 7,502,217 | B2 | 3/2009 | Zhao et al. |
| 7,561,917 | B2 | 7/2009 | Wegrzyn, III et al. |
| 7,564,674 | B2 | 7/2009 | Frysz et al. |
| 7,630,768 | B1 | 12/2009 | Coffed et al. |
| 7,706,124 | B2 | 4/2010 | Zhao et al. |
| 7,720,538 | B2 | 5/2010 | Janzig et al. |
| 7,736,191 | B1 | 6/2010 | Sochor |
| 7,742,817 | B2 | 6/2010 | Malinowski et al. |
| 7,747,321 | B2 | 6/2010 | Fischbach et al. |
| 7,761,165 | B1 | 7/2010 | He et al. |
| 7,765,005 | B2 | 7/2010 | Stevenson |
| 7,794,256 | B1 | 9/2010 | Sochor |
| 7,930,032 | B2 | 4/2011 | Teske et al. |
| 7,989,080 | B2 * | 8/2011 | Greenberg et al. ......... 428/472.2 |
| 8,000,804 | B1 | 8/2011 | Wessendorf et al. |
| 8,065,009 | B2 | 11/2011 | Biggs |
| 8,131,369 | B2 | 3/2012 | Taylor et al. |
| 8,163,397 | B2 * | 4/2012 | Ok et al. ..................... 428/472.2 |
| 8,288,654 | B2 | 10/2012 | Taylor et al. |
| 8,346,362 | B2 | 1/2013 | Kinney et al. |
| 8,391,983 | B2 | 3/2013 | Lim |
| 8,494,635 | B2 * | 7/2013 | Troetzschel et al. ............ 607/37 |
| 8,497,435 | B2 | 7/2013 | Nagata et al. |
| 8,528,201 | B2 * | 9/2013 | Troetzschel et al. ............ 29/851 |
| 8,656,736 | B2 * | 2/2014 | Terao ............................. 65/59.1 |
| 8,742,268 | B2 | 6/2014 | Reisinger et al. |
| 2001/0013756 | A1 | 8/2001 | Mori et al. |
| 2004/0116976 | A1 | 6/2004 | Spadgenske |
| 2004/0128016 | A1* | 7/2004 | Stewart ........................ 700/159 |
| 2006/0247714 | A1 | 11/2006 | Taylor et al. |
| 2006/0259093 | A1 | 11/2006 | Stevenson et al. |
| 2007/0183118 | A1 | 8/2007 | Fu et al. |
| 2008/0119906 | A1 | 5/2008 | Starke |
| 2008/0203917 | A1 | 8/2008 | Maya |
| 2008/0269831 | A1 | 10/2008 | Erickson |
| 2009/0192578 | A1 | 7/2009 | Biggs |
| 2009/0281586 | A1 | 11/2009 | Lim |
| 2010/0023086 | A1 | 1/2010 | Lim |
| 2010/0109966 | A1 | 5/2010 | Mateychuk et al. |
| 2010/0258342 | A1 | 10/2010 | Parker |
| 2011/0034965 | A1* | 2/2011 | Troetzschel et al. ............ 607/37 |
| 2011/0034966 | A1* | 2/2011 | Troetzschel et al. ............ 607/37 |
| 2011/0186349 | A1* | 8/2011 | Troetzschel et al. .......... 174/650 |
| 2012/0127627 | A1 | 5/2012 | Brendel et al. |
| 2012/0193117 | A1 | 8/2012 | Specht et al. |
| 2012/0193118 | A1* | 8/2012 | Kempf et al. .............. 174/50.53 |
| 2012/0193119 | A1 | 8/2012 | Kempf et al. |
| 2012/0193125 | A1 | 8/2012 | Pavlovic et al. |
| 2012/0193141 | A1 | 8/2012 | Reisinger et al. |
| 2012/0194981 | A1 | 8/2012 | Kempf et al. |
| 2012/0197326 | A1 | 8/2012 | Pavlovic |
| 2012/0197327 | A1 | 8/2012 | Specht |
| 2012/0197335 | A1 | 8/2012 | Reisinger |
| 2012/0197368 | A1 | 8/2012 | Reisinger |
| 2012/0200011 | A1 | 8/2012 | Pavlovic |
| 2012/0203294 | A1* | 8/2012 | Troetzschel ...................... 607/5 |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |
| EP | 1754511 | 2/2007 |
| WO | 03073450 | 9/2003 |
| WO | 2004110555 | 12/2004 |
| WO | 2008103166 | 8/2008 |
| WO | 2010091435 | 8/2010 |

OTHER PUBLICATIONS

The Office Action for U.S. Appl. No. 13/361,340 mailed Oct. 25, 2013 (20 pages).
The Restriction Requirement for U.S. Appl. No. 13/361,348 mailed Nov. 14, 2013 (7 pages).
The Office Action for U.S. Appl. No. 13/361,355 mailed Aug. 7, 2013 (21 pages).
The Restriction Requirement for U.S. Appl. No. 13/361,362 mailed Nov. 14, 2013 (7 pages).
The Office Action for U.S. Appl. No. 13/361,370 mailed Oct. 29, 2013 (26 pages).
The Restriction Requirement for U.S. Appl. No. 13/361,374 mailed Mar. 5, 2013 (6 pages).
The Office Action for U.S. Appl. No. 13/361,374 mailed Oct. 4, 2013 (22 pages).
The Restriction Requirement for U.S. Appl. No. 13/361,383 mailed Feb. 27, 2013 (6 pages).
The Office Action for U.S. Appl. No. 13/361,383 mailed Nov. 13, 2013 (22 pages).
The Restriction Requirement for U.S. Appl. No. 13/361,404 mailed Apr. 8, 2013 (6 pages).
The Restriction Requirement for U.S. Appl. No. 13/361,404 mailed Oct. 9, 2013 (5 pages).
The Notice of Allowance for U.S. Appl. No. 13/361,355 mailed Jan. 16, 2014 (18 pages).
The Office Action for U.S. Appl. No. 13/361,322 mailed date Feb. 19, 2014 (26 pages).
The Office Action for U.S. Appl. No. 13/361,340 mailed date Apr. 29, 2014 (18 pages).
The Office Action for U.S. Appl. No. 13/361,348 mailed date Feb. 19, 2014 (23 pages).
The Office Action for U.S. Appl. No. 13/361,362 mailed date Feb. 19, 2014 (19 pages).

(56) References Cited

OTHER PUBLICATIONS

The Office Action for U.S. Appl. No. 13/361,370 mailed date May 14, 2014 (18 pages).
The Office Action for U.S. Appl. No. 13/361,374 mailed date May 1, 2014 (20 pages).
The Notice of Allowance for U.S. Appl. No. 13/361,383 mailed date Apr. 25, 2014 (18 pages).
The Office Action for U.S. Appl. No. 13/361,388 mailed date Feb. 11, 2014 (24 pages).
The Office Action for U.S. Appl. No. 13/361,404 mailed date Feb. 27, 2014 (19 pages).
The Restriction Requirement for U.S. Appl. No. 13/361,411 mailed date Mar. 10, 2014 (7 pages).

* cited by examiner

METHOD FOR THE MANUFACTURE OF A CERMET-CONTAINING BUSHING

CROSS-REFERENCE TO RELATED APPLICATIONS

This Non-Provisional patent application claims the benefit of the filing date of U.S. Provisional Patent Application Ser. No. 61/438,057, filed Jan. 31, 2011, entitled "METHOD FOR THE MANUFACTURE OF A CERMET-CONTAINING BUSHING," and this patent application also claims priority to German Patent Application No. DE 10 2011 009 861.5, filed on Jan. 31, 2011, and both of which are incorporated herein by reference.

CROSS-REFERENCE TO RELATED APPLICATIONS

This patent application is also related to patent application Ser. No. 13/361,322 filed on Jan. 30, 2012, entitled "CERAMIC BUSHING FOR AN IMPLANTABLE MEDICAL DEVICE"; patent application Ser. No. 13/361,340 filed on Jan. 30, 2012, entitled "DIRECTLY APPLICABLE ELECTRICAL BUSHING"; patent application Ser. No. 13/361,348 filed on Jan. 30, 2012, entitled "IMPLANTABLE DEVICE HAVING AN INTEGRATED CERAMIC BUSHING"; patent application Ser. No. 13/361,355 filed on Jan. 30, 2012, entitled "HEAD PART FOR AN IMPLANTABLE MEDICAL DEVICE"; patent application Ser. No. 13/361,362 filed on Jan. 30, 2012, entitled "CERMET-CONTAINING BUSHING FOR AN IMPLANTABLE MEDICAL DEVICE HAVING A CONNECTING LAYER"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE"; patent application Ser. No. 13/361,374 filed on Jan. 30, 2012, entitled "CERAMIC BUSHING WITH FILTER"; patent application Ser. No. 13/361,383 filed on Jan. 30, 2012, entitled "CERAMIC BUSHING WITH INDUCTIVE FILTER"; patent application Ser. No. 13/361,388 filed on Jan. 30, 2012, entitled "CERAMIC BUSHING HAVING HIGH CONDUCTIVITY CONDUCTING ELEMENTS"; patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE"; and patent application Ser. No. 13/361,411 filed on Jan. 30, 2012, entitled "CERMET-CONTAINING BUSHING WITH HOLDING ELEMENT FOR AN IMPLANTABLE MEDICAL DEVICE".

BACKGROUND

One aspect relates to a method for the manufacture of an electrical bushing for use in a housing of an active implantable medical device.

The post-published document, DE 10 2009 035 972, discloses an electrical bushing for an implantable medical device having the features of the preamble of claim 1. Moreover, a use of at least one cermet-comprising conducting element in an electrical bushing for an implantable medical device and a method for the manufacture of an electrical bushing for an implantable medical device are disclosed.

A multitude of electrical bushings for various applications are known, examples including: U.S. Pat. No. 4,678,868, U.S. Pat. No. 7,564,674 B2, US 2008/0119906 A1, U.S. Pat. No. 7,145,076 B2, U.S. Pat. No. 7,561,917, US 2007/0183118 A1, U.S. Pat. No. 7,260,434B1, U.S. Pat. No. 7,761,165, U.S. Pat. No. 7,742,817 B2, U.S. Pat. No. 7,736,191 B1, US 2006/0259093 A1, U.S. Pat. No. 7,274,963 B2, US 2004116976 A1, U.S. Pat. No. 7,794,256, US 2010/0023086 A1, U.S. Pat. No. 7,502,217 B2, U.S. Pat. No. 7,706,124 B2, U.S. Pat. No. 6,999,818 B2, EP 1754511 A2, U.S. Pat. No. 7,035,076, EP 1685874 A1, WO 03/073450 A1, U.S. Pat. No. 7,136,273, U.S. Pat. No. 7,765,005, WO 2008/103166 A1, US 2008/0269831, U.S. Pat. No. 7,174,219 B2, WO 2004/110555 A1, U.S. Pat. No. 7,720,538 B2, WO 2010/091435, US 2010/0258342 A1, US 2001/0013756 A1, DE 10 2008 021 064 A1, US 2008/0119906 A1, U.S. Pat. No. 7,260,434, U.S. Pat. No. 4,315,054, and EP 0877400.

DE 697 297 19 T2 describes an electrical bushing for an active implantable medical device—also called implantable device or therapeutic device. Electrical bushings of this type serve to establish an electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one of its sides. Said connection body includes a hollow space having at least one connection socket for connecting electrode leads. In this context, the connection socket includes electrical contacts in order to electrically connect the electrode leads to the control electronics on the interior of the housing of the implantable therapeutic device. Hermetic sealing with respect to a surrounding is an essential prerequisite of an electrical bushing of this type. Therefore, lead wires that are introduced into an electrically insulating base body—also called conducting elements—through which the electrical signals are propagated, must be introduced into the base body such as to be free of gaps. In this context, it has proven to be challenging that the lead wires generally are made of a metal and are introduced into a ceramic base body. In order to ensure durable connection between said two elements, the internal surface of a through-opening—also called openings—in the base body is being metallized in order to attach the lead wires by soldering. However, the metallization in the through-opening has proven to be difficult to apply. Only cost-intensive procedures ensure homogeneous metallization of the internal surface of the bore hole—and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally correspond

DETAILED DESCRIPTION

Figure 1:
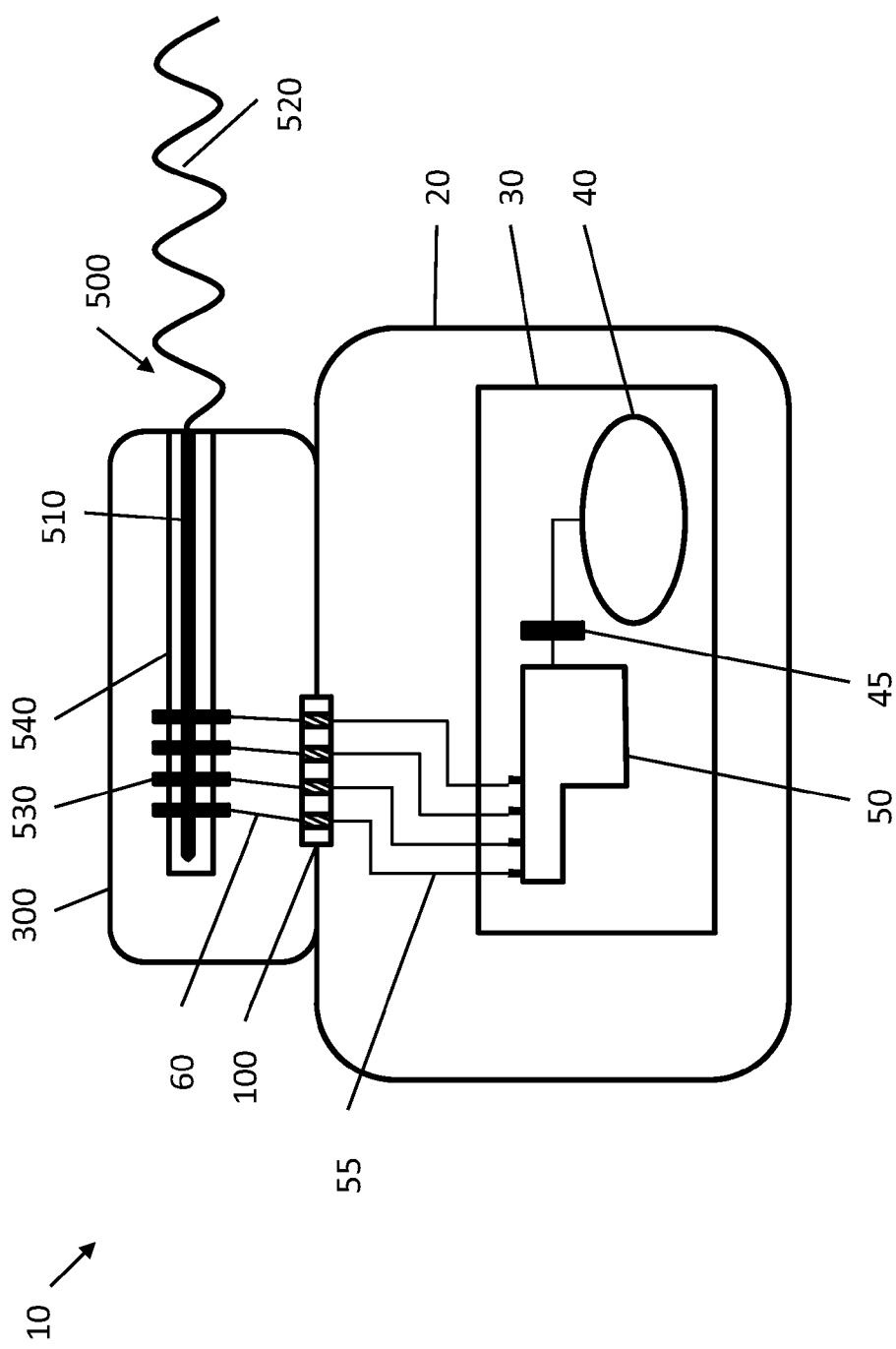
- FIG. 1 illustrates an active implantable medical device.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment provides a method for the manufacture of an electrical bushing for use in a housing of an active implantable medical device, in which the above-mentioned disadvantages are overcome, at least in part, in one embodiment, in that a durable sealing connection between base body and conducting element is ensured. One embodiment provides for the manufacture of an electrical bushing for an active implantable medical device.

One embodiment relates to a method for the manufacture of an electrical bushing for use in a housing of an active implantable medical device, whereby the electrical bushing includes at least one electrically insulating base body and at least one electrical conducting element, whereby the conducting element is set-up to establish, through the base body, at least one electrically conducting connection between an internal space of the housing and an external space, whereby the conducting element is hermetically sealed with respect to the base body, whereby the at least one conducting element includes at least one cermet. One embodiment provides the method to include the following steps:

forming a base body green compact having a through-opening that extends through the base body green compact from a ceramic slurry or a ceramic powder;

generating at least one conducting element green compact from a cermet slurry or a cermet powder;

producing a bushing blank by combining the at least one conducting element green compact and the base body green compact; and separating the bushing blank into at least two electrical bushings.

The disadvantages according to the prior art are overcome, in part, in the scope of the method according to one embodiment in that both the base body and the conducting element are made from a material based on a ceramic material. The manufacturing method described herein utilizes this in order to render the manufacture of the electrical bushing inexpensive and simple. In this context, a hermetically sealed connection between the conducting element and the base body is established, without the base body and the conducting element needing to be connected to each other in the scope of further procedural steps, such as soldering. In this context, the similarity of the starting materials that are used for base body and conducting element—a cermet and a ceramic material—guarantees that a durable, firmly bonded connection is established that prevents the ingress of environmental influences through the electrical bushing and into the active implantable medical device in an effective and durable manner. As a precautionary note, it shall be mentioned that the procedural steps described herein can be carried out in virtually any conceivable order. The sequence of the procedural steps shall not be defined by the sequence listed herein.

The proposed electrical bushing is set-up for use in an implantable medical device, that is, for application in an implantable medical device, whereby the implantable medical device can be provided, for example, as an active implantable medical device (AIMD) and in one embodiment as a therapeutic device.

As a matter of principle, the term, implantable medical device, shall include any device which is set-up to perform at least one medical function and which can be introduced into a body tissue of a human or animal user. As a matter of principle, the medical function can include any function selected from the group consisting of a therapeutic function, a diagnostic function, and a surgical function. The medical function can, for example, include a function, in which at least one stimulus is exerted on the body tissue, for example, an electrical stimulus. Said stimulating function can be exerted, for example, by means of at least one stimulus generator and/or by means of at least one stimulus transmitter, for example by means of an actuator. However, other types of exerting a stimulus are also feasible as a matter of principle.

As a matter of principle, the term, active implantable medical device—also called AIMD—shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, includes at least one housing, for example, at least one hermetically sealed housing. The housing can in one embodiment enclose at least one electronics unit, for example a triggering and/or analytical electronics unit of the implantable medical device.

According to the scope of one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element with respect to strains occurring during operation and/or upon handling, and/or provide protection to the functional element with respect to ambient influences such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can include at least one hollow space which can be closed fully or in part. However, alternatively, the internal space can be filled up fully or in part, for example by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing and/or, for example, the electrical bushing can, for example, be provided to be hermetically sealed such that, for example, the internal space, is hermetically sealed with respect to the external space. In this context, the term, "hermetically sealed", can illustrate that moisture and/or gases cannot permeate through the hermetically sealed element at all or only to a minimal extent upon intended use for the common periods of time (for example 5-10 years). The so-called leak rate, which can be determined, for example, by leak tests, is a physical parameter that can describe, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of one embodiment, said maximal permissible helium leak rates can, for example, be from $1 \times 10^{-8}$ atm*cm$^3$/sec to $1 \times 10^{-7}$ atm*cm$^3$/sec. In the scope of one embodiment, the term, "hermetically sealed", shall be understood, for example, to mean that the device to be tested (for example the housing and/or the electrical bushing and/or the housing with the electrical bushing) has a helium leak rate of less than $1 \times 10^{-7}$ atm*cm$^3$/sec. In one embodiment, the helium leak rate can be less than $1 \times 10^{-8}$ atm*cm$^3$/sec, in one embodiment, less than $1 \times 10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

Electrical bushings are elements set-up to create at least one electrically conducting path that extends between the internal space of the housing to at least one external point or region outside the housing, for example, situated in the external space. Accordingly, this establishes an electrical connection to leads, electrodes, and sensors that are arranged outside the housing, for example.

Common implantable medical devices are commonly provided with a housing, which can include, on one side, a head part, also called header or connecting body, that carries connection sockets for connection of leads, also called electrode leads. The connection sockets include, for example, electrical contacts that serve to electrically connect the leads to a control electronics unit on the interior of the housing of the medical device. Usually, an electrical bushing is provided in the location, at which the electrical connection enters into the housing of the medical device, and the electrical bushing is inserted into a corresponding opening of the housing in a hermetically sealing manner.

Due to the type of use of implantable medical devices, their hermetic sealing and biocompatibility are usually amongst the foremost requirements. The implantable medical device proposed herein according to one embodiment, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device, and thus the electrical bushing as well, should be as impermeable as possible, for example, with respect to body fluids.

Moreover, the electrical bushing should ensure high electrical insulation between the at least one conducting element and the housing and/or the multiple conducting elements provided that more than one conducting element are present. In this context, the insulation resistance reached in one embodiment is at least several MOhm, in one embodiment, more than 20 MOhm, and the leakage currents reached can be small, in one embodiment, less than 10 pA. Moreover, in case multiple conducting elements are present, the crosstalk and electromagnetic coupling between the individual conducting elements in one embodiment are below the specified thresholds for medical applications.

The electrical bushing disclosed according to in one embodiment is well-suited for the above-mentioned applications. Moreover, the electrical bushing can also be used in other applications that are associated with special requirements with regard to biocompatibility, tight sealing, and stability.

The electrical bushing according to in one embodiment can meet, for example, the above-mentioned tight sealing requirements and/or the above-mentioned insulation requirements.

The electrical bushing and/or the base body and/or the conducting element can, as a matter of principle, be of any shape, for example a round shape, an oval shape or a polygonal shape, for example, a rectangular or square shape.

As mentioned above, the electrical bushing includes at least one electrically insulating base body. In the scope of one embodiment, a base body shall be understood to mean an element that serves a mechanical holding function in the electrical bushing, for example in that the base body holds or carries the at least one conducting element either directly or indirectly. For example, the at least one conducting element can be embedded in the base body directly or indirectly, fully or partly, for example, through a firmly bonded connection between the base body and the conducting element and in one embodiment through co-sintering of the base body and the conducting element. For example, the base body can have at least one side facing the internal space and at least one side facing the external space and/or accessible from the external space.

The base body can, for example, be designed to be rotationally symmetrical about an axis, for example about an axis that is arranged to be essentially perpendicular to the housing opening. Accordingly, the base body can have the shape of a disc, for example a disc with a round, oval or polygonal base surface. Alternatively, the base body may just as well have a graduated shape, for example a shape of at least two discs of different diameters or equivalent diameters that are placed one on the other, which in one embodiment are in a concentric arrangement with respect to each other and which, for example, can have a round, an oval or a polygonal, for example, rectangular or square, cross-section. However, other designs are also feasible as a matter of principle.

As mentioned above, the base body is provided to be electrically insulating. This means that the base body, fully or at least regions thereof, is made from at least one electrically insulating material. For example, the at least one electrically insulating material can be arranged such that the at least one conducting element is electrically insulated with respect to the housing and/or, if multiple conducting elements are provided, that these are electrically insulated with respect to each other. In this context, an electrically insulating material shall be understood to mean a material with a resistivity of at least $10^2$ Ohm*m, in one embodiment, of at least $10^6$ Ohm*m, in one embodiment of at least $10^{10}$ Ohm*m, and in one embodiment of at least $10^{12}$ Ohm*m. For example, the base body can be provided such that, as mentioned above, a flow of current between the conducting element and the housing and/or between multiple conducting elements is prevented, at least largely, for example through the resistivity values between the conducting element and the housing as specified above being implemented. For example, the base body can include at least one ceramic material.

In this context, a conducting element or electrical conducting element shall generally be understood to mean an element set-up to establish an electrical connection between at least two sites and/or at least two elements. For example, the conducting element can include one or more electrical conductors, for example metallic conductors. In the scope of one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side of the base body and/or electrical bushing facing the internal space or on a side of the base body and/or electrical bushing facing the external space or accessible from the external space, one or more connecting contacts, for example one or more plug-in connectors, for example one or more connecting contacts, which project from the base body or can be electrically contacted through other means from the internal space and/or the external space. The conducting element can, for example, can, on the side of the base body facing the internal space, end flush with the base body and/or project from the base body into the internal space or be connected to another element. Regardless of the design of the inside, this applies just as well to the side of the base body facing the external space.

The at least one conducting element can establish the electrically conductive connection between the internal space and the external space in a variety of ways. For example, the conducting element can extend from at least one section of the conducting element that is arranged on the side of the base body facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other.

The electrical bushing according to in one embodiment can include a frame element. In the scope of in one embodiment, a frame element shall be understood to mean an element set-up to serve as connecting element between the base body and the housing and to allow the base body to be fixed in place in or on the housing. The fixation can be effected fully or partly inside and/or outside the housing and/or partly or fully within an opening of the housing. The housing opening, in turn, can have any cross-section as a matter of principle, for example a round, oval or polygonal shape, for example, a rectangular or square shape. For example, the frame element can be designed such as to effect a connection between the base body and the housing to be hermetically sealed, in one embodiment in such a manner that the housing opening is closed and the frame element is hermetically sealed through the base body.

As mentioned above, the frame element is designed as a metallic frame element, that is, it is fully or partly made from at least one metallic material. In one embodiment, the frame element is free of ceramic materials. The frame element can, for example, surround the base body fully or in part. Accordingly, the frame element can, for example, be ring-shaped having at least one frame opening, into which the base body can project for example, or in which the base body is taken up fully or partly for example, and which is in one embodiment hermetically sealed through the base body.

The electrically insulating base body can support, as a bearing, and/or surround, at least in part, for example, the at least one conducting element. For example, the at least one conducting element can be embedded in the base body fully or partly, for example in a firmly bonded manner. The at least one material of the base body should in one embodiment be biocompatible, as illustrated above, and should have sufficiently high insulation resistance. It has proven to be advantageous for the base body according to one embodiment to include at least one ceramic material or to consist of at least one ceramic material. In one embodiment, the base body includes one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium(CE, Ti) oxide, and sodium-potassium-niobate.

With regard to possible refinements of the cermet and/or metal materials and/or components that are used, reference shall be made to the embodiments specified above. Combinations of multiple possibilities specified above are conceivable as well. In this context, ZTA shall be understood to mean zirconium-toughened alumina (Zirkonia Toughened Alumina), that is, a material, in which zirconium oxide is embedded in an aluminum oxide matrix, for example 10-30% by volume zirconium dioxide in an aluminum oxide matrix. In this context, ATZ shall be understood to mean alumina-toughened zirconia, that is, a material, in which aluminum oxide is embedded in a zirconium oxide matrix, for example at a fraction of 10-30% by volume. Y-TZP shall be understood to mean yttrium-toughened zirconium oxide, that is, zirconium oxide comprising an yttrium fraction. KNN means potassium-sodium niobate.

The base body can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors with no ceramic fraction.

In the scope of one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added. The ceramic powder or powders of the cermet in one embodiment have a mean grain size of less than 10 µm, in one embodiment less than 5 µm, and in one embodiment less than 3 µm. The metallic powder or powders of the cermet in one embodiment have a mean grain size of less than 15 µm, in one embodiment less than 10 µm, and in one embodiment less than 5 µm. For production of a base body, for example, at least one ceramic powder can be used to which, for example, at least one binding agent and, if applicable, at least one solvent can be added. In this context, the ceramic powder or powders of the base body in one embodiment has/have a mean grain size of less than 10 µm (1 µm corresponds to 1*10E-6 m), in one embodiment less than 5 µm, and in one embodiment less than 3 µm. For example, the median value or the d50 value of the grain size distribution is considered to be the mean grain size in this context. The d50 value corresponds to the value at which 50 percent of the grains of the ceramic powder and/or metallic powder are finer and 50% are coarser than the d50 value.

In the scope of one embodiment, a ceramic manufacturing method shall be understood to mean a procedure that includes at least one sintering process of at least one insulating and/or at least one electrically conductive material, for example, at least one ceramic material. As shall be explained in more detail below, said ceramic manufacturing method can, for example, include a forming for the manufacture of at least one form body, for example one ceramic green compact and/or at least one ceramic brown compact.

In the scope of the one embodiment, a sintering or a sintering process shall generally be understood to mean a procedure for the manufacture of materials or work-pieces, in which powdered, for example, fine-grained, ceramic and/or metallic substances are heated and connected in the process. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, for example, at least 100 bar, or even at least 1000 bar. The process can proceed, for example, fully or partly, at temperatures below the melting temperature of the powdered materials, for example at temperatures of 700° C. to 1400° C. The process can be carried out, for example, fully or partly, in a tool and/or a mold such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

The electrical bushing according to one embodiment can be manufactured in a method comprising the following steps:

a. manufacturing the at least one base body and introducing the at least one conducting element into the base body in non-sintered or pre-sintered condition;

b. joint sintering of the base body and conducting element.

Accordingly, a sintered condition is understood to mean a condition of a work-piece, in which the work-piece has already undergone one or more steps of sintering. Accordingly, a non-sintered condition is understood to mean a condition, in which the work-piece has not yet undergone a step of sintering. In this condition, the work-piece can for example be present as a green compact. A pre-sintered condition shall be understood to mean a condition, in which the work-piece has already undergone at least one step of sintering or at least one part of a step of sintering, in which the work-piece has not been sintered completely though, that is, in which the work-piece can still be sintered further and can be sintered further through one or more steps of sintering. In this condition, the work-piece can be present, for example, as at least partial green compact, as brown compact or already as a ceramic body.

A method can be used, for example, in the manufacture of the at least one conducting element and/or optionally in the manufacture of the at least one base body, in which at least one green compact is manufactured first, subsequently at least one brown compact is manufactured from said green compact, and subsequently the finished work-piece is manufactured from said brown compact through at least one sintering step. In this context, separate green compacts and/or separate brown compacts can be manufactured for the conducting element and the base body and can be connected subsequently. Alternatively, one or more common green compacts and/or brown compacts can be produced for the base body and the conducting element. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, one or more binding materials. A brown compact shall be understood to mean a pre-form body which is generated from the green compact through at least one debinding step, for example at least one thermal and/or chemical debinding step, whereby the at least one binding agent and/or the at least one solvent is/are removed, at least partly, from the pre-form body in the debinding step.

The sintering process, for example, of a cermet, but of the base body just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the bushing according to one embodiment, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate.

For the bushing according to one embodiment, the at least one metallic component of the cermet can include, for example, at least one of the following metals and/or an alloy based on at least one of the following metals: platinum, iridium, niobium, molybdenum, tantalum, tungsten, titanium, cobalt or zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content in one embodiment should be 25% by volume and more, in one embodiment 32% by volume, in one embodiment, more than 38% by volume, depending on which materials have been selected.

In the scope of one embodiment, the terms, "including a cermet," "cermet-including," "comprising a cermet," and "cermet-containing", are used synonymously. Accordingly, the terms refer to the property of an element, being that the element contains cermet. This meaning also includes the variant of an embodiment in that elements, for example the conducting element, consist of a cermet, that is, are fully made of a cermet.

In one embodiment, both the at least one conducting element and the base body can include one or more components which are or can be manufactured in a sintering procedure, or the at least one conducting element and the base body are or can both be manufactured in a sintering procedure. For example, the base body and the conducting element are or can be manufactured in a co-sintering procedure, that is, a procedure of simultaneous sintering of these elements. For example, the conducting element and the base body each can include one or more ceramic components that are manufactured, and in one embodiment compacted, in the scope of at least one sintering procedure.

For example, a base body green compact can be manufactured from an insulating composition of materials. This can proceed, for example, by compressing the composition of materials in a mold. In this context, the insulating composition of materials advantageously in one embodiment is a powder mass, in which the powder particles illustrate at least minimal cohesion. In this context, the manufacture of a green compact proceeds, for example, through compressing powder masses and/or through forming followed by drying.

Said procedural steps can also be utilized to form at least one cermet-containing conducting element green compact. In this context, one embodiment can provide that the powder, which is compressed to form the conducting element green compact, is cermet-containing or consists of a cermet or includes at least one starting material for a cermet. Subsequently, the two green compacts—the base body green compact and the conducting element green compact—can be combined. The manufacture of the conducting element green compact and of the base body green compact can just as well proceed simultaneously, for example, by multi-component injection molding, co-extrusion, etc., such that there is no longer a need to connect them subsequently.

While the green compacts are being sintered, they are in one embodiment subjected to a heat treatment below the melting temperature of the powder particles of the green compact. This usually leads to compaction of the material and thus to ensuing substantial reduction of the porosity and volume of the green compacts. Accordingly, in the method of one embodiment the base body and the conducting element can be sintered jointly. Accordingly, there is in one embodiment no longer a need to connect the two elements subsequently.

Through the sintering, the conducting element becomes connected to the base body in one embodiment in a positive fit-type and/or non-positive fit-type and/or firmly bonded manner. In one embodiment achieves hermetic integration of the conducting element into the base body. In one embodiment, there is no longer a need for subsequent soldering or welding of the conducting element into the base body. Rather, a hermetically sealing connection between the base body and the conducting element is attained through the joint sintering in one embodiment and utilization of a cermet-containing green compact in one embodiment.

One refinement of the method according to one embodiment is characterized in that the sintering includes only partial sintering of the at least one optional base body green compact, whereby said partial sintering can effect and/or include, for example, the debinding step described above. In one embodiment, the green compact is heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to its/their final size. In the scope of said variant of an embodiment, the green compact is in one embodiment sintered only partly in order to attain a certain stability to render the green compact easier to handle.

The starting material used for producing at least one conducting element green compact and/or at least one base body green compact can, for example, be a dry powder or include a dry powder, whereby the dry powder is compressed in the dry state into a green compact and illustrates sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available, for example. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be shaped into a green compact without the application of high pressure.

In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the work-piece.

Thermoplastic and duroplastic polymers, waxes, thermogelling substances and/or surface-active substances, for example, can be used as binding agent—also called binder. In this context, these can be used alone or as binding agent mixtures of multiple components of this type. If individual elements or all elements of the electrical bushing (for example the at least one base body green compact and/or the at least one conducting element green compact) are produced in the scope of an extrusion procedure, the composition of the binding agent should be such that the line of the elements extruded through the nozzle is sufficiently stable in shape for the shape defined by the nozzle to be maintained easily. Suitable binders, also called binding agents, are known to the person skilled in the art.

A conducting element provided according to one embodiment with at least one cermet can be connected easily to other structural elements, since it is a composite of metal and ceramic material. Accordingly, green compacts of both the conducting element and other structural elements, for example in the base body, can be produced and subsequently subjected to a sintering process. Alternatively or in addition, at least one common green compact for multiple structural elements can be manufactured just as well. The resulting electrical bushing is not only particularly biocompatible and durable, but also possesses good hermetic sealing properties. Thus, usually no fissures or connecting sites still to be soldered arise between the conducting element and the base body. Rather, sintering results in the base body and the conducting element becoming connected. One embodiment provides the at least one conducting element to consist of a cermet. In this variant of an embodiment, the conducting element includes not only components made of cermet, but is fully made of a cermet.

Generally, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing bearing element can proceed, for example, alike a process for homogeneous powders except that, at identical compression force, the metal is usually compacted more strongly than the ceramic material. Compared to sintered hard metals, the cermet-containing conducting element usually illustrates higher resistance to thermal shock and oxidation. As explained above, the ceramic components can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate. The at least one metallic component can include, for example, at least one of the following metals and/or an alloy based on at least one of the following metals: platinum, a platinum alloy, iridium, niobium, molybdenum, titanium, a titanium alloy, cobalt, zirconium, chromium, tantalum, a tantalum alloy, tungsten, a tungsten alloy.

There are multiple ways of connecting the electrical bushing to a housing. Accordingly, one option is to directly connect the electrical bushing to the housing, for example in a positive fit-type manner and/or non-positive fit-type manner and/or firmly bonded manner. For example, a firmly bonded connection between the frame element and an inside and/or an outside of the housing and/or an edge of the housing facing in the direction of the housing opening can be implemented, for example, at least one soldered connection. In order to promote the wetting of the electrical bushing, for example, of the ceramic base body of the electrical bushing, with solder, at least one metallization of the base body can be provided, for example a metallization that is applied through at least one vapor deposition procedure, for example a sputtering procedure. Said metallization can, for example, include at least one metal selected from the group consisting of gold, titanium and chromium and/or at least one combination and/or at least one multiple layer comprising one or more of said metals.

The frame element is a component of the electrical bushing and can be provided, for example, in a condition, in which the frame element is already connected to the base body. Alternatively, the frame element can just as well be connected to the base body only during the manufacture of the implantable medical device, whereby said connecting can be effected before, during or after connecting the frame element to the housing.

As mentioned above, the at least one frame element can be provided in order to fix the base body in place in the at least one housing opening of the housing. Said at least one frame element is designed as metallic frame element. The frame element can be designed, for example, as a closed or partly open frame that encloses the at least one optional frame opening. The base body can be attached to the housing through a single frame element or, just as well, through multiple frame elements.

The frame element can, for example, act as a holding element or be designed, fully or in part, as a holding element. The frame element can, for example, include at least one flange, whereby the flange can, for example, be electrically conductive. The purpose of the flange can be to seal the electrical bushing with respect to a housing of the implantable device. The frame element in one embodiment holds the electrical bushing in the housing. The frame element can, for example, include at least one flange on at least one external side, for example on the circumferential side. Said flange can form a bearing, which, for example, is engaged by the housing of the implantable medical device or parts thereof, for example lids and/or housing shells, in one embodiment engaged in a sealing manner. Accordingly, the frame element having the at least one flange attached can have, for example, a U-, T-, L- or H-shaped cross-section. Integrating at least one flange into the frame element ensures that the electrical bushing is integrated into the implantable device in a safe, impact-resistant and durable manner. In addition, the flange can be designed such that the housing or parts thereof can be connected to it in a positive fit-type manner and/or non-positive fit-type manner, for example through at least one clip-like connection.

According to another aspect, the in one embodiment proposes an implantable medical device having the features described above. Features and details that were described in the context of the electrical bushing and/or any of the methods shall also apply in relation to the implantable medical device, and vice versa. Moreover, the implantable medical device can further include, for example, at least one supply lead, which is also called "lead" or "leads" in English and can be set-up to form an electrical connection to the electrical bushing, for example an electrical plug connection. The lead can, for example, include at least one plug element, for example at least one male and/or at least one female plug element, which can form an electrical plug-in connection with the plug connection element of the electrical bushing. This can, for example, be at least one male plug element which can be plugged into the at least one plug connection element, for example at least one plug element according to the IS-1 (ISO 5841-3), DF-1 (ISO 11318:1993) and/or IS-4 standard.

The housing includes the at least one housing opening. The housing opening can basically be of any shape, for example a round, oval or polygonal shape. The housing can, for example, be assembled from multiple housing parts, for example from at least two housing shells, whereby, for example, the housing opening is accommodated in one of the housing parts or in at least two of the housing parts, for example in the form of cut-outs in the housing parts which complement each other to form the housing opening when the housing parts are joined. The housing can, for example, be manufactured fully or in part from a metallic material, in one embodiment from titanium or a titanium alloy. Alternatively or in addition, any other materials can be used just as well, for example one or more of the materials specified above with regard to the frame element.

At least one electrical connection between at least one internal space of the housing and at least one external space is established through the electrical bushing. The housing opening can be closed, for example, and as specified above, in a hermetically sealed manner by the electrical bushing.

The proposed electrical bushing, the implantable medical device, and the methods some embodiments provide a large number of advantages as compared to known devices and methods of the specified type. Accordingly, a cost-efficient manufacturing method can be implemented which features high process reliability and low waste production at the same time. For example, according to one embodiment, the number of boundary surfaces can be reduced which allows the potential of errors to be generally reduced. The boundary surfaces being reduced reduces, for example, the ingress of moisture or body fluid. Simultaneously, the use of ceramic materials allows high mechanical stability and strong sealing against moisture, for example, body fluid, to be implemented. Accordingly, the proposed bushings have a long service life. Simultaneously, unlike in conventional methods, a plurality of procedural steps can be combined and, optionally, automated in the scope of customary ceramic manufacturing procedures.

As part of the investigations, the following exemplary embodiment of an electrical bushing according to one embodiment would be produced: In the first step, a cermet mass is produced from platinum (Pt) and aluminum oxide (Al2O3) containing 10% zirconium dioxide (ZrO2). The following starting materials are used for this purpose:

40 vol. % Pt powder with a mean grain size of 10 μm, and
60 vol. % Al2O3/ZrO2 powder with a relative ZrO2 content of 10% and a mean grain size of 1 μm.

The two components were mixed, water and a binding agent were added, and the sample was homogenized through a kneading process. Analogous to the first step, a ceramic mass is produced in a second step from a powder with an Al2O3 content of 90% and a ZrO2 content of 10%. The mean grain size was approx. 1 μm. As before, water and a binding agent were added to the ceramic powder and the sample was homogenized. In a third step, the ceramic mass made of aluminum oxide with a 10% zirconium dioxide content produced in step two was converted to the shape of a base body. A cermet body, which was made from the cermet mass produced in step 1 and contained a mixture of platinum powder and aluminum oxide with a zirconium dioxide content of 10%, was introduced as green compact into an opening in the base body green compact. Subsequently, the ceramic mass was compacted in the mold. Then the cermet and the ceramic component were subjected to debinding at 500° C. and the sintering was finished at 1650° C.

The scope of the method according to one embodiment includes a step of forming a base body green compact and a step of producing at least one conducting element green compact. Said steps can be carried out in parallel or in any sequential order. Moreover, the green compact formed or generated first can support the subsequent steps of generating or forming the respective second green compact. The green compact is generated mainly through mechanical compaction of the ceramic material or cermet material, for example, of the powder or slurry. This often necessitates a mold, into which the slurry or powder is pressed. This aspect results in multiple variants of embodiments for the sequence of the individual procedural steps of the manufacturing method according to one embodiment:

Accordingly, the base body green compact can be formed first in the scope of one method. This can be effected, for example, by mechanical compression of the ceramic slurry and/or ceramic powder. According to one embodiment, the base body green compact includes at least one through-opening that extends through it. The through-opening in the base body green compact can form a kind of mold for the second step of generating the conducting element green compact. The scope of this variant of an embodiment provides that the cermet slurry and/or the cermet powder and/or the metal component of the cermet is introduced, for example, dosed, into the through-opening, in one embodiment is dosed by means of a micro-dosing system, and compressed therein, for example, by hand. Accordingly, the through-opening serves as the mold that serves as the mold for mechanical compression of the cermet slurry and/or cermet powder. The conduction element green compact is generated by compression within the through-opening in the base body green compact. In this variant of an embodiment, it is particularly expedient that the cermet slurry and/or the cermet powder is provided to be pasty, that is, as an, for example, doughy tough mass. A cermet-containing paste is easy and simple to introduce into the through-opening and to compress therein, for example, by hand. Introducing the cermet-containing paste—which includes a cermet slurry and/or a cermet powder—ensures, for example, that no fissures, gaps or other hollow spaces arise between the conducting element green compact and the base body green compact thus generated, which would possibly prevent a firmly bonded sintered connection between the conducting element and the base body from being established.

In another embodiment, the conducting element green compact is generated first. Subsequently, the conducting element green compact can be over-molded with a pasty ceramic slurry and/or ceramic powder in one embodiment. In this context, the conducting element green compact serves as a negative mold around which the base body green compact is built up.

In the scope of another variant of an embodiment, the base body green compact and the at least one conducting element green compact are produced separately. This can be effected by compression or any other known methods. In this context, producing the bushing blank in the scope of the combining includes introducing the at least one conducting element green compact into the at least one through-opening of the base body green compact. The mechanical stability of the green compacts allows them to be slid in, for example, allows the conducting element green compact to be slid into the through-opening. Subsequently, a firmly bonded connection is established between the conducting element green compact and the internal wall of the through-opening of the base body green compact in the scope of the later sintering. In order to promote this, the clearances between the conducting element green compact and the diameter of the through-opening caused by the shrinking process in the scope of the sintering should not exceed predetermined limits. This ensures that a firmly bonded connection between the conducting element green compact and the base body green compact can be established.

It shall be noted in this context that a thermal treatment is not absolutely required in order to produce the green compact. Depending on the binding agent provided, mechanical pressure is sufficient to produce a green compact.

According to the scope of one embodiment, the step of combining the conducting element green compact and the base body green compact therefore does not necessarily include that both exist separately. One embodiment also includes that the conducting element green compact and/or the base body green compact is produced only during the step of combining in the scope of the production of the bushing blank. For example, the first two of the methods described above suggest said interpretation of the procedural steps described herein.

A variant of an embodiment of the method is characterized in that the base body green compact and the conducting element green compact are sintered separately before the bushing blank is produced. This may produce, for example, brown compacts from the green compacts. In the scope of said variant of an embodiment, the two basic elements of the electrical bushing—the base body and the conducting element—are sintered spatially separately at the green compact stage. Accordingly, both parts are at least partly sintered when they are joined in the scope of producing the bushing blank. In order to attain the desired firmly bonded connection between the conducting element and the base body, either another sintering step can be carried out after the step of producing the bushing blank or said sintering step can be carried out only after the step of separating the bushing blank into at least two electrical bushings.

An alternative method provides the bushing blank to be sintered after being produced. In this variant of an embodiment, the at least one conducting element green compact is integrated into the base body green compact in order to produce a bushing blank made up of green compacts. Then, the first sintering is carried out in which a firmly bonded connection is built up between the conducting element and the base body, at least partly. As before, the green compacts can be converted into brown compacts. Said sintering step can proceed to the extent that completely sintered electrical bushings are produced upon separation of the bushing blank. Alternatively, it is feasible that complete sintering of the electrical bushing occurs in a second sintering step only after separation of the bushing blank. The variant of an embodiment of the method according to one embodiment described here is expedient, for example, if the conducting element green compacts can be slid or introduced into the through-openings of the base body both easily and without any damage. During the subsequent sintering step, an extended firmly bonded connection between the insulating base body and the electrically conductive conducting element is established along the inside of the through-opening. Said firmly bonded sintered connection between the base body and the at least one conducting element ensures that the electrical bushing is hermetically sealed.

Another variant of an embodiment is characterized in that the at least two electrical bushings are sintered after the step of separating the bushing blank into at least two electrical bushings.

Another variant of an embodiment is characterized in that the step of forming and/or producing and/or generating proceeds in the scope of at least one of the following procedures: uniaxial pressing, cold isostatic pressing, hot isostatic pressing, injection molding or an extrusion procedure, for example, a co-extrusion procedure.

Extrusion involves that viscous curable materials, such as, for example, ceramic materials, are pressed through a suitably shaped nozzle in a continuous procedure. This results in bodies of any length whose cross-section corresponds to that of the nozzle. In some of these procedures, the extrudate is first melted by an extruder—also called screw extruder—by means of heating and/or internal friction, and, if applicable, homogenized. Moreover, the pressure needed for flowing through the nozzle is built up in the extruder. The extrudate solidifies after it exits from the nozzle. The effect of applying a vacuum is that the profile is pressed against the gauging wall and the step of forming is thus completed. Often, a cooling path is provided downstream of this step. The cross-section of the geometrical body thus produced corresponds to the nozzle or gauging that is used. The step of combining like or unlike materials before they exit from the profile nozzle is also called co-extrusion. There are one-stage and two-stage procedures in this context:

One-stage procedures: In the one-stage process, also called direct extrusion, the 2 materials that are processed concurrently are guided to the extruder in the same place and at the same time.

Two-stage procedures: In the two-stage extrusion process, the materials to be processed are first mixed and compacted in parallel twin-screw extruders (compounders), heating/cooling mixers or pelleting presses. The actual extrusion then occurs in a separate apparatus that is directly coupled or spatially and temporally separated.

A variant of the method according to one embodiment is characterized in that the ceramic slurry or the ceramic powder is pressed through a first nozzle in order to form the base body green compact. This type of forming is called extruding. In addition, the cermet slurry and/or cermet powder can be pressed through a second nozzle in order to generate the at least one conducting element green compact. The purpose of the conducting elements is to conduct electrical signals and they generally are cylinder-like in shape. Shapes of this type can be manufactured easily through extruding processes and/or through the utilization of suitably designed nozzles through which the cermet slurry or the cermet powder is pressed like a dough. The slurries or powders are compacted inside the first and/or second nozzle described above. Compaction and, if applicable, the use of a binding agent then generate the respective green compact.

Another variant of an embodiment is characterized in that the steps of forming and generating proceed in spatial proximity and/or in the scope of the step of producing. Depending on the manufacturing method of the green compacts, it may be advantageous in one embodiment that the base body green compact and the conducting element green compact are manufactured such that both are combined close to the time they are produced. The step of combining of this type is feasible, for example, in co-extrusion procedures. In co-extrusion procedures, the steps of forming and generating can proceed in close spatial proximity, for example by pressing the slurries or powders through a first and second nozzle. In this context, the step of producing is associated directly with the steps of forming and generating. The at least one conducting element green compact is introduced into the base body green compact right after it is generated such that the bushing blank is produced right away. Said variant of an embodiment enables rapid and inexpensive production of larger bushing element blanks and thus of a larger number of electrical bushings.

Another variant of an embodiment is characterized in that the separating includes a disaggregating or a cutting or a chipping with a geometrically defined or undefined cutting form, or a stripping. In the scope of one embodiment, "separating" shall refer to the generic term for shape changes. Cutting is a chip-less forming of a material in a cutting tool through a cutting punch and cutting plate (so-called cutting tools). According to DIN 8588, disaggregating is the partial or full separation of a body or system into two or more parts. Disaggregating procedures share that they process the material mechanically without forming chips. Chipping involves a relative motion of the cutting wedge of a tool and the workpiece to initially swage and later remove as chips the particles above a wedge cutting path upon advancing penetration.

The utilization of a parallel manufacturing method, such as extruding, disclosed herein results in a total of four variants of an embodiment for the sequence of the individual procedural steps of the manufacturing method:

a) In this variant, initially, the initial step of forming the base body green compact and the at least one conducting element green compact proceeds while they are spatially separate. Subsequently, said parts are being partly sintered. After this follows the step of producing the bushing blank, in which the conducting element green compact is combined with the through-opening of the base body, for example, is introduced into the through-opening. Subsequently, another sintering step and the step of separating the bushing blank into at least two electrical bushings are carried out. The sequence of the two latter steps can also be reversed.

b) Said variant of an embodiment differs from variant a) in that the green compacts, in their raw condition, are combined to form the bushing blank prior to the first sintering step. Accordingly, this involves no separate partial sintering of the green compacts prior to the step of producing the bushing blank.

c) In the scope of said variant of an embodiment, the steps of forming and generating are carried out directly in the scope of the step of preparing, such as is enabled, for example, through an extruding procedure. Subsequently, a step of sintering of the bushing blank and subsequent step of separating into the at least two electrical bushings are carried out.

d) Said variant of an embodiment differs from variant c) in that, after the step of producing the bushing blank, same is first separated into the at least two electrical bushings and a sintering only follows thereafter.

In order to produce a larger number of electrical bushings inexpensively and rapidly, it has proven advantageous in one embodiment that the bushing blank is separated into a plurality of bushings. Said separation of the bushing blank can proceed in parallel or sequentially.

After completion of the sintering, in one embodiment at least one surface of the electrical bushing is polished and contacted to a metallic pin or wire at least one site of the surface at which a conducting element is arranged. The step of contacting can be effected by soldering. The step of contacting is effected through metallic wires or pins. Alternatively, the bushing body can just as well be provided to project beyond the electrical bushing and/or the base body and form a contacting pin itself. A flow of current from one side of the bushing body to the other is provided through this means.

In the electrical bushing according to one embodiment, a hermetically firmly bonded sintered connection exists due to the sintering process of the adjoining bodies and provides not only a desired transition from electrically insulating to electrically conductive, but also a desired impermeability for gases and liquids.

The electrical bushing manufactured according to one embodiment mainly serves for transmitting electrical signals out of the implantable device. These can, for example, be stimulation pulses that are conducted to the heart muscle through an appropriately designed lead. However, modern implantable devices also include leads that are provided with a sensor in order to collect medical information, for example from heart muscle, and transmit this information to the implantable device. Accordingly, there is often a need to have a plurality of electrically conductive conducting elements to be arranged in an electrical bushing. Utilization of the bushing provided according to one embodiment ensures that the electrical signals flowing through the electrically conductive conducting elements do not interfere with each other. Accordingly, another variant of an embodiment is characterized in that the bushing includes multiple conducting elements and a corresponding number of through-openings. Depending on the design, the electrical bushing can include 16, 32, 64 or 128 separate conducting elements that are arranged to be separate from each other in an electrically insulating base body. In this context, it has proven to be advantageous in one embodiment that the longitudinal axes of the conducting elements extend essentially parallel to each other. Depending on the application field, the conducting elements can be evenly distributed on a straight line or multiple straight lines that extend parallel to each other. In special applications, it has also proven to be advantageous that the conducting elements are evenly distributed over a circular arc that extends to be concentric with respect to the base body.

Another variant of an embodiment of the method according to one embodiment is characterized by the following step:

Introducing a filter element in order to change a signal conducted by the at least one conducting element as a function of its frequency and/or amplitude and/or phase.

The effect of the lead of the implantable device on electromagnetic signals is that of an antenna. Known sources of interference, such as the mobile phone network, can therefore induce currents in the leads of the implantable device. Said currents can then flow through the electrical lead into the implantable device and damage the electronics unit therein. It has proven to be advantageous in one embodiment for preventing this damage to integrate a filter element into the electrical bushing. The purpose of said filter element is to change, for example, to attenuate, electrical signals that may be induced. In this context, the attenuation depends on the frequency and/or amplitude and/or phase of the electrical signal. In a variant of an embodiment, the filter element includes at least one capacitor, whereby the capacitor includes electrodes and the electrodes are electrically connected in alternating manner to at least one of the conducting elements and the housing of the active implantable medical device. One embodiment is characterized in that the electrical bushing further includes at least one filter element, for example, a filter element selected from the group consisting of: a high-pass filter, a low-pass filter, a band-pass filter.

FIG. 1 illustrates an active implantable medical device 10. The electrical bushing 100 is part of said device 10. Device 10 includes a housing 20. A circuit board 30 is arranged inside the housing 20 and has an electronics unit 50 installed on it. A battery 40 supplies the needed electrical energy to the electronics unit 50. A capacitor 45 can be used to store the pulse energies required for implantable defibrillators. The electrical bushing 100 according to one embodiment is integrated into the housing 20 in such a manner that the electronics unit 50 is sealed-off hermetically from the surroundings. The electrical bushing 100 according to one embodiment allows helium leak rates of less than $1\times10^{-9}$ atm*cm$^3$/sec to be attained. Moreover, it withstands cleaning and sterilization processes.

The individual channels of the electronics unit 50 are connected to the individual conducting elements 110 of the electrical bushing 100 through internal connecting elements 55. Said internal connecting elements 55 can be wires and/or sintered elements that are connected directly to the electronics unit 50. In case the implantable medical device 10 is a cardiac pacemaker, the electronics unit 50 is to trigger pulses which are conducted through a lead 500 to an electrode (not illustrated here) which in general is arranged to be situated right in the patient's heart muscle. In this location, the electrical pulse of the cardiac pacemaker can stimulate the heart muscle. The electrical bushing 100 is part of said lead that conducts the electrical pulse from the electronics unit 50 to the electrode. The actual lead 500 that is introduced into the patient's body includes a lead wire 520 that extends through parts of the patient and is connected, on its distal end, to the electrode. On the proximal end, the lead wire 520 is connected to a connection plug 510. Said connection plug 510 is supported, as in a bearing, in a receiving element 540. The receiving element 540 is part of a head part 300—also called header—that is connected to the housing 20 of the implantable device 10. In known implantable devices, said head part 300 is manufactured from a plastic material. Multiple connecting sockets 530 are arranged inside the receiving element 540 and establish a non-positive type- and/or positive type— contact to the connection plug 510. In addition, the connecting sockets 530 are connected through external connecting elements 60 to the conducting elements 110 in the electrical bushing 100. On one inside within the housing 20, the conducting elements 110 are electrically connected through internal connecting elements 55 to the individual channels of the electronics unit 50 of the implantable device 10. Accordingly, an electrical pulse from the electronics unit 50 can be conducted through the internal connecting elements 55, through the conducting elements 110, the external connecting elements 60, and the connection socket 530 to the electrode and thus to the heart muscle.

Figure 2:
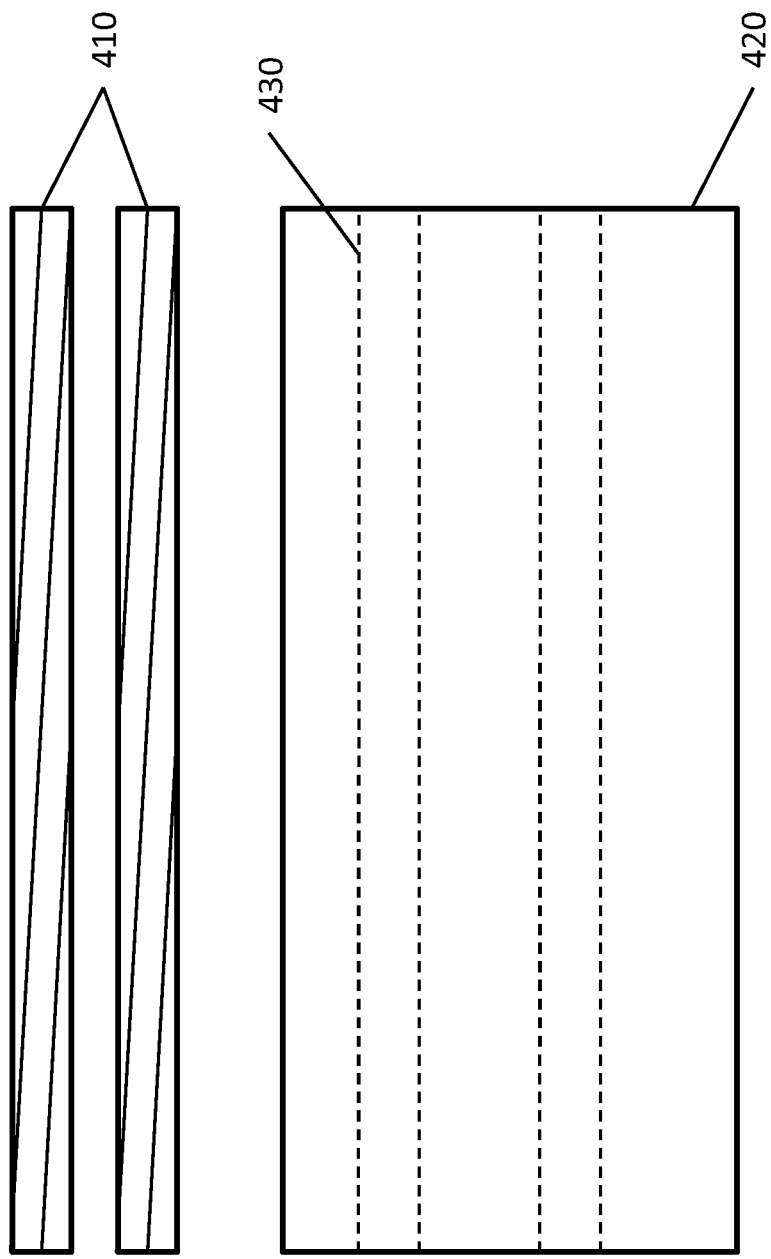
FIG. 2 illustrates a base body green compact and two conducting element green compacts.

Two conducting element green compacts 410 are illustrated in FIG. 2. These are generated from a cermet slurry or a cermet powder. Said step of generating can be effected in that a cermet slurry or cermet powder is pressed into a mold while applying an external pressure. Said mold then reflects the external shape of the conducting element green compact 410. In addition, FIG. 2 illustrates a base body green compact 420. Said base body green compact 420 has been formed from a ceramic slurry or a ceramic powder. The step of forming the base body green compact 420 can be effected by a plurality of methods, whereby extruding methods, for example, have proven to be advantageous in one embodiment. In the example illustrated, both green compacts 410, 420 were formed and/or generated separately. Depending on how the slurry or powder materials used herein are provided, the base body green compact 420 and/or the conducting element green compact 410 can already be partially sintered at this time, for example, both can have reached the stage of a brown compact.

This attains, for example, increased mechanical stability. The base body green compact 420 can be manufactured from a ceramic slurry or ceramic powder with electrically insulating properties. In addition, through-openings 430 are integrated into the base body green compact 420. The through-opening does not necessarily have to extend fully through the base body green compact 420. However, it has proven to be advantageous in one embodiment if this is the case. This is so because the conducting element green compact has to be integrated into the through-opening 430 in order to produce the electrically conductive conducting element according to one embodiment later-on, during the step of preparing the bushing blank and/or electrical bushings. The conducting element 100 ensures that an electrical signal is conducted from one side of the electrical bushing 10 to the other side of the electrical bushing 10, that is, establishes, in an assembly stage, an electrically conductive connection between an internal space of the housing 20 and an external space.

Figure 3:
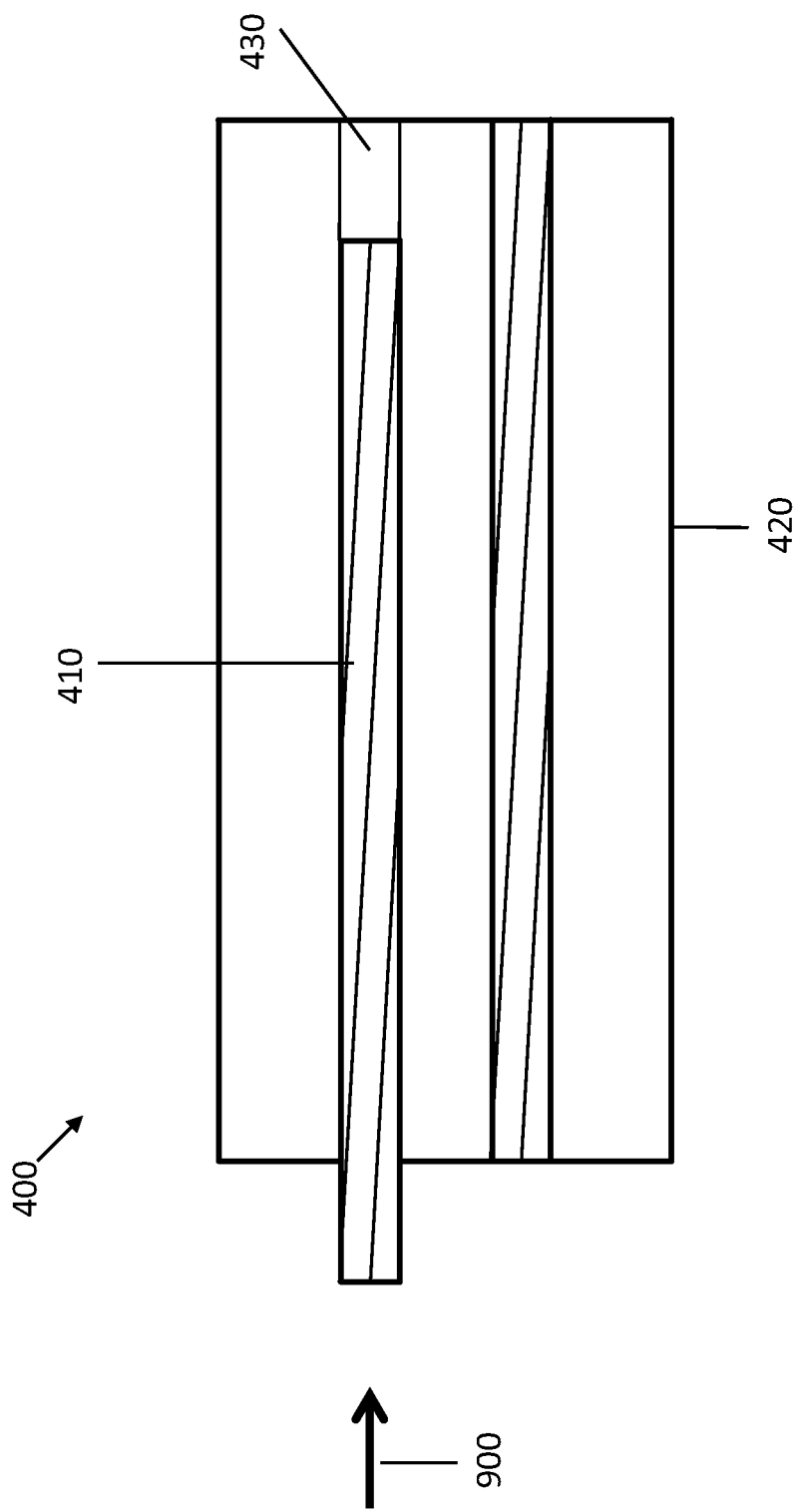
FIG. 3 illustrates an integration of the conducting element green compacts into two through-openings of the base body green compact.
Figure 4:
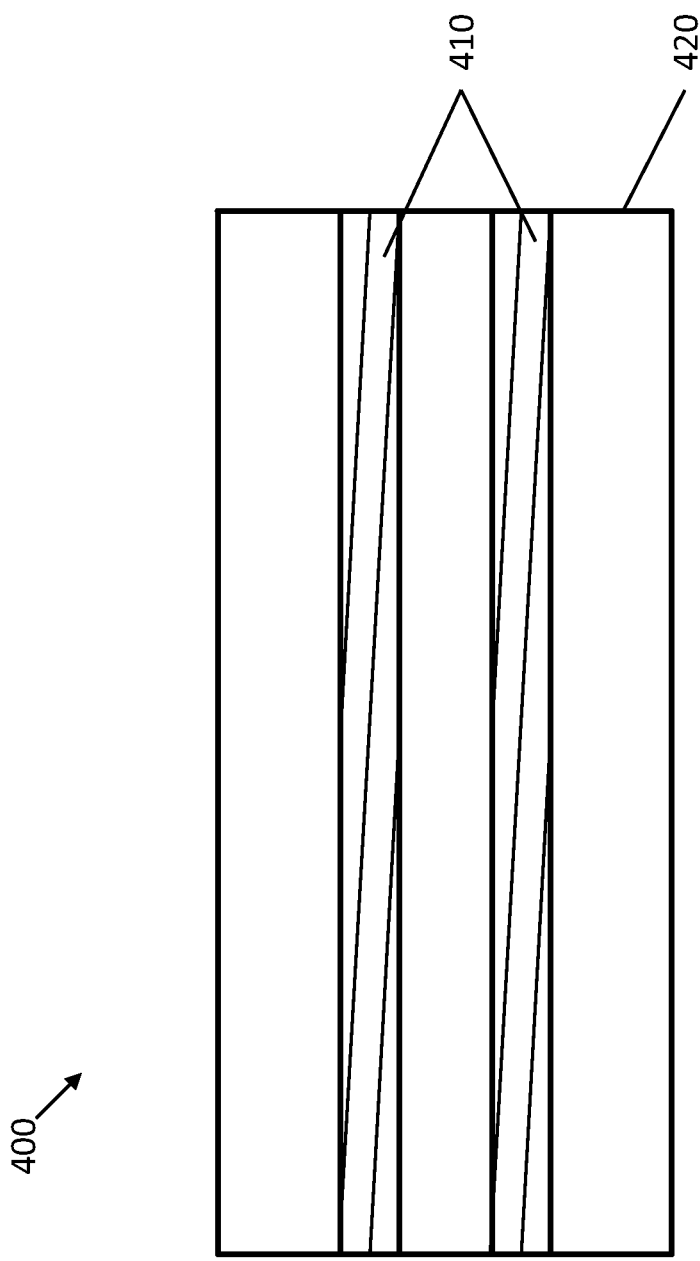
FIG. 4 illustrates a bushing blank.

FIG. 3 illustrates the step of preparing a bushing blank 400. As indicated here through the motion arrow 900, the conducting element green compacts 410 are slid into the through-openings 430 of the base body green compact 420. Following said step of combining the conducting element green compacts 410 and the base body green compact 420, a bushing blank 400 is thus produced, which includes two conducting element green compacts 410 in parallel arrangement in the exemplary embodiment illustrated. In this context, the bushing element blank 400 has a geometrical length that is multiple times larger than the geometrical length of an electrical bushing 100. Once the two conducting element green compacts 410 are fully slid into the through-openings 430, the finished bushing blank 400 illustrated in FIG. 4 is made. Depending on the variant of an embodiment, said bushing blank 400 can be subjected to another sintering step.

Figure 5:
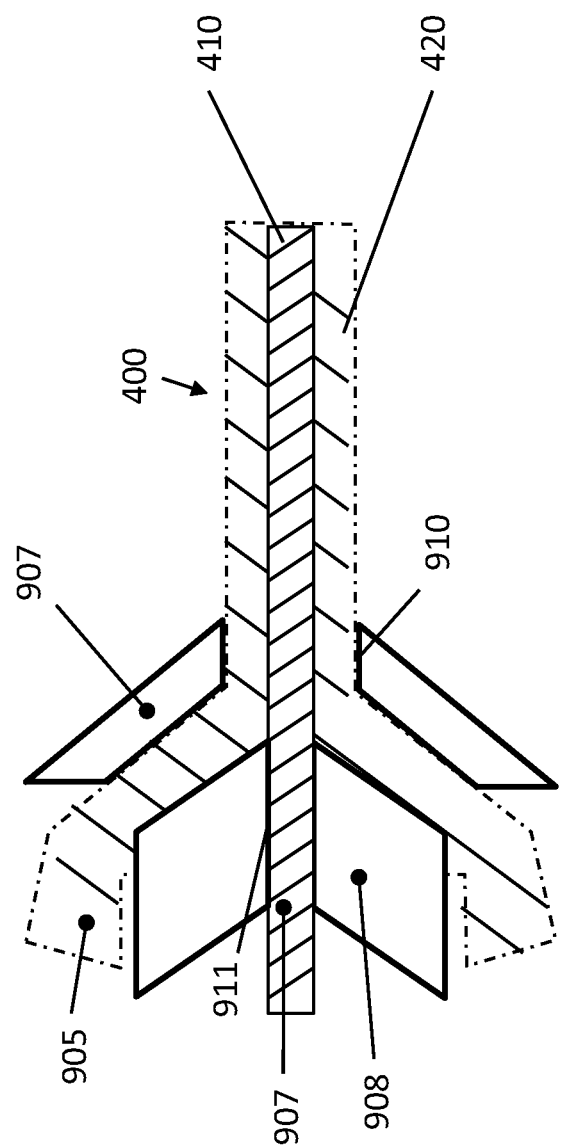
FIG. 5 illustrates a schematic view of a co-extrusion method.

A variant of an embodiment of the method according to in one embodiment provides that the steps of forming the base body green compact and generating the at least one conducting element green compact proceed in spatial proximity and in the scope of the step of producing the bushing blank 400. FIG. 5 schematically illustrates some elements of a device for co-extruding the two above-mentioned green compacts 410, 420. A ceramic slurry 905 is pressed through a first nozzle 906 in the exemplary embodiment illustrated. The first nozzle 906 includes a nozzle opening 910. The geometrical shape thereof determines the external shape of the base body green compact 420 which exits in the form of a strand from the first nozzle 906. A conveying mechanism (not illustrated here) is used to ensure that the ceramic slurry 905 is conveyed and pressed into the first nozzle 906. A cermet powder 907 is pressed into a second nozzle 908 separate from the ceramic slurry 905. The second nozzle opening 911 thereof determines the external contour of the conducting element green compact 410. The second nozzle 908 simultaneously serves as rear wall and is therefore part of the first nozzle 906. The arrangement of the first nozzle illustrated here ensures that the ceramic slurry 905 encloses the conducting element green compact 410 that exits from the second nozzle opening 911 and that both green compacts 410,420 exit from the first nozzle 806 jointly and thus form the bushing blank 400. The cermet powder 907 is conveyed in the direction of the second nozzle 908 through a conveying mechanism that is not illustrated here. The coextruding system being illustrated in FIG. 5 is to illustrate schematically how the step of generating the conducting element green compact 410 and base body green compact 420 can proceed concurrently to the simultaneous production of the bushing blank 400. Obviously, it is feasible to adapt the co-extruding procedure suitably such that a plurality of conducting element green compacts 410 is produced to be introduced into a base body green compact 420.

Figure 6:
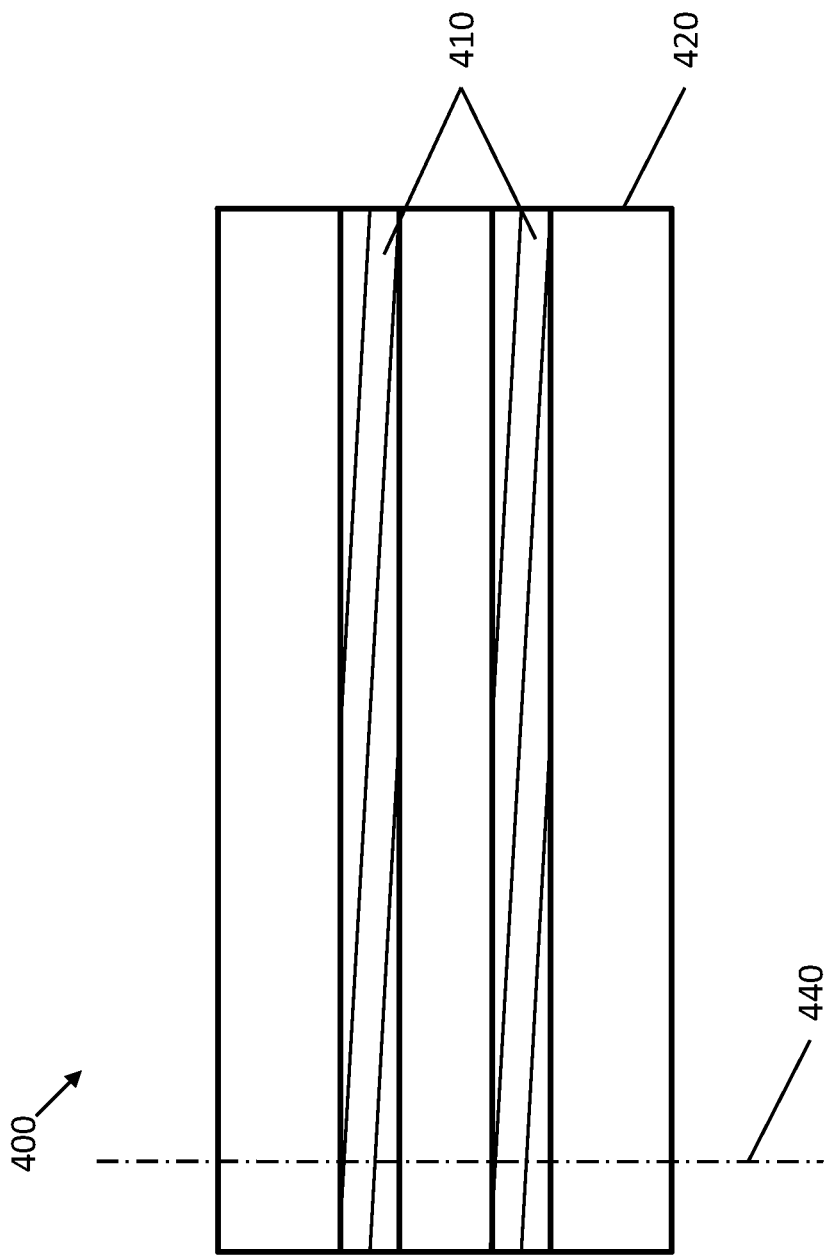
FIG. 6 illustrates a step of separating an electrical bushing from the bushing blank.
Figure 7:
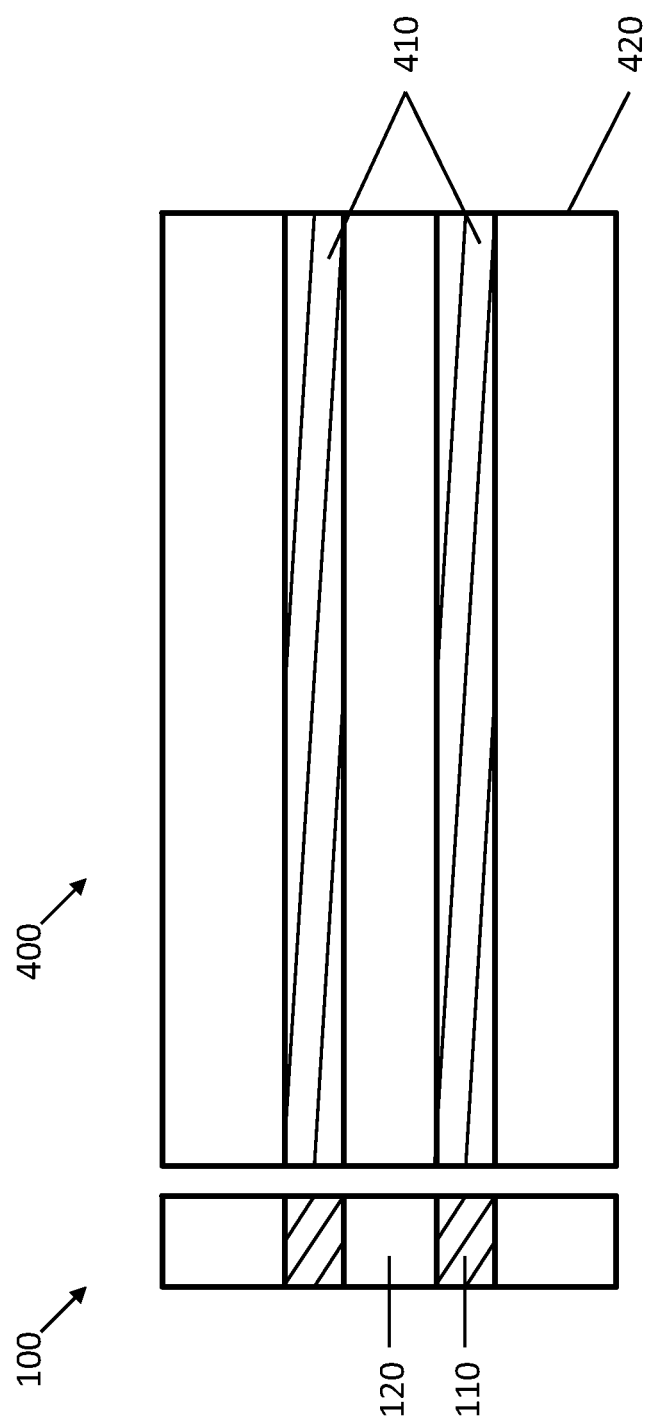
FIG. 7 illustrates a separated electrical bushing.

FIG. 6 illustrates the bushing blank 400. The figure also illustrates a sectional line 440 along which an electrical bushing 100 is to be separated from the bushing blank 400. In this context, the step of separating can be designed in the scope of a variety of processes. Accordingly, steps of disintegrating, cutting or chipping are feasible depending on whether the bushing blank 400 is not sintered, partially sintered or fully sintered. Other factors influencing the step of separating include the materials that are used for the green compacts as well as geometrical requirements pertaining to the electrical bushing. After the step of separating, an electrical bushing 100 is generated that can be used for an active implantable medical device 10—as is illustrated in FIG. 7. Said electrical bushing 100 includes an electrically insulating base body 120 and, in the exemplary embodiment illustrated, two electrically conductive conducting elements 110. In this context, one embodiment provides the conducting element to extend through the base body 120 and to be sealed hermetically in the base body 120. As detailed above, the purpose of the conducting element 410 is to conduct electrical signals through the base body 120. Accordingly, there is a need for the conducting element 110 to be contactable from at least two sides of the base body. Moreover, the conducting element 110 must be integrated into the base body 120 in a hermetically sealed manner. This is attained in one embodiment through joint sintering of the base body green compact 420 and conducting element green compact 410 such that a firmly bonded connection between the conducting element 110 and the base body 120 is attained. Said firmly bonded connection does not have to be established throughout the entire length of the conducting element 110 in the base body.

Figure 8:
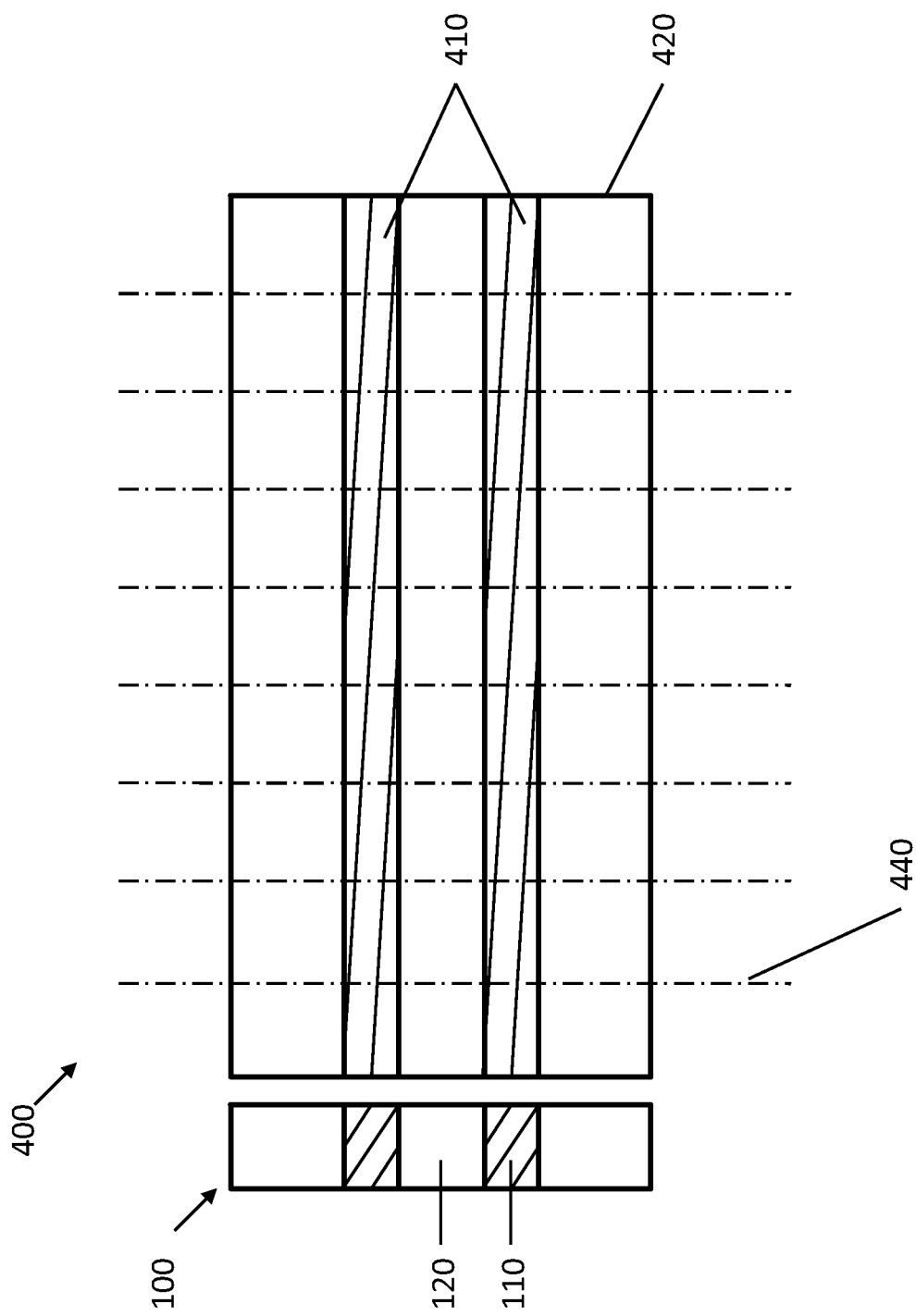
FIG. 8 illustrates a step of parallel separation of a plurality of electrical bushings.
Figure 9:
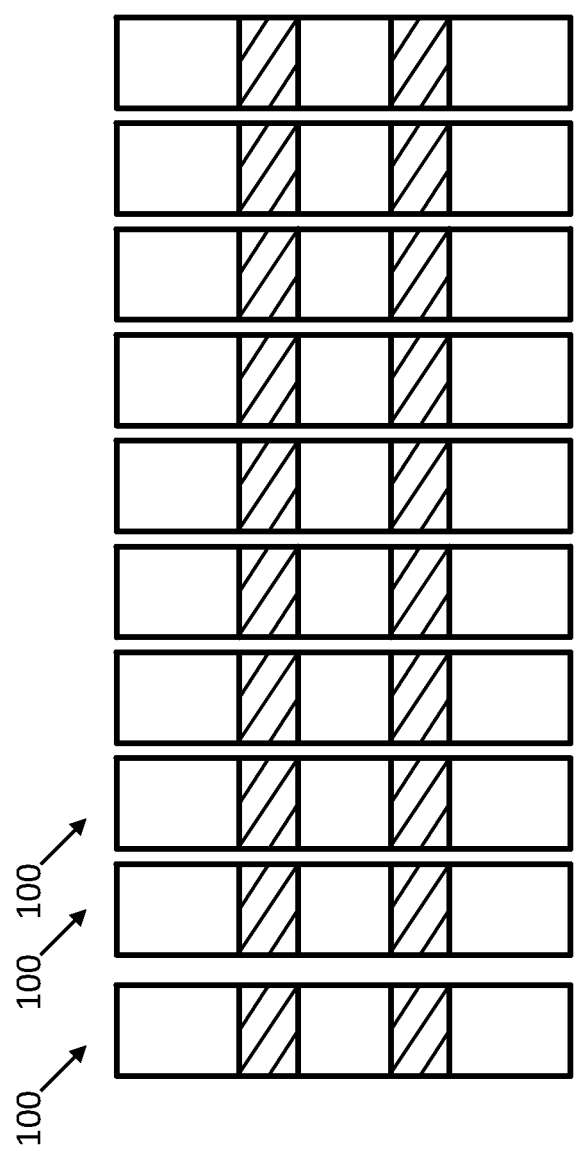
FIG. 9 illustrates a plurality of said electrical bushings.

The purpose of FIGS. 8 and 9 is to illustrate the step of separating the bushing blank 400 into a plurality of bushings 100. Said division can proceed concurrently or sequentially in this context. Placing appropriate cuts along the separation lines 440, the bushing blank 400 is divided into a plurality of identically shaped electrical bushings 100. The manufacture of a plurality of bushings 100 is thus ensured to be simple and inexpensive.

Figure 10:
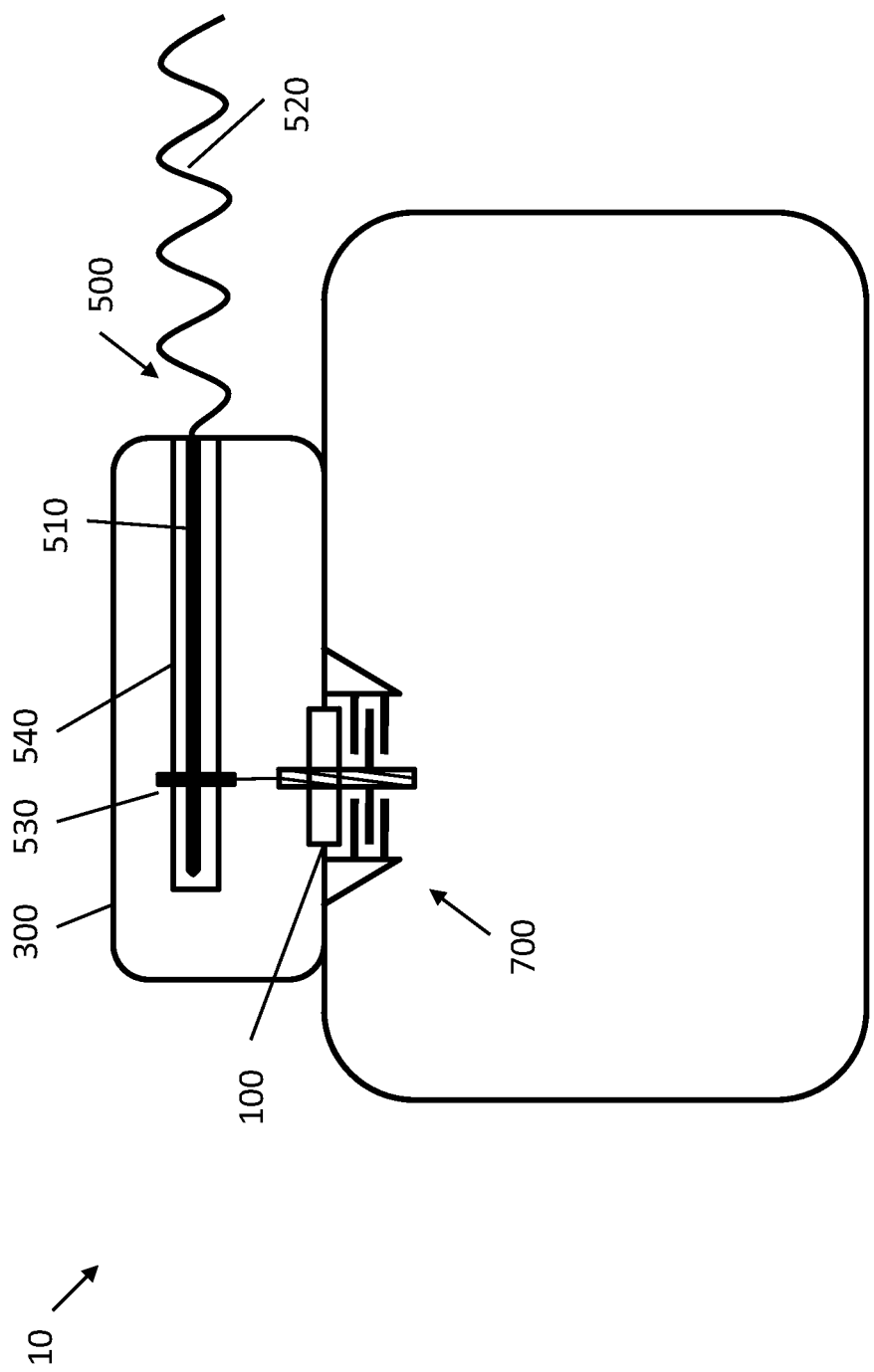
FIG. 10 illustrates an active implantable medical device having a filter element.

Another procedural step according to one embodiment is characterized by the introduction of a filter element 700. FIG. 10 illustrates a schematic view of a filter element of this type. It shall be noted that the arrangement of the filter as well as its size have been selected only for purposes of schematic presentation in FIG. 10. The filter element 700 can obviously be part of the electrical bushing. It has proven to be advantageous in one embodiment that parts of the filter element are introduced into the base body green compact and thus enable concurrent sintering and/or firmly bonded connection of the base body green compact 420 to the filter element 700. The purpose of the filter element 700 is to change and/or attenuate electrical signals conducted by the conducting element as a function of their frequencies, amplitudes or phases.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for the manufacture of an electrical bushing for use in a housing of an active implantable medical device,
   whereby the electrical bushing comprises at least one electrically insulating base body and at least one electrical conducting element;
   whereby the conducting element is set-up to establish, through the base body, at least one electrically conductive connection between an internal space of the housing and an external space;
   whereby the conducting element is hermetically sealed with respect to the base body;
   whereby the at least one conducting element comprises at least one cermet;
   characterized in that the method comprises:
      forming a base body green compact having a through-opening that extends through the base body green compact from a ceramic slurry or a ceramic powder;
      generating at least one conducting element green compact from a cermet slurry or a cermet powder;
      producing a bushing blank by combining the at least one conducting element green compact and the base body green compact; and
      separating the bushing blank into at least two electrical bushings;
      characterized in that the base body green compact and the conducting element green compact are sintered separately before the bushing blank is produced, the step of producing the bushing blank is effected by introducing the at least one conducting element green compact in the at least one through-opening of the base body green compact.

2. A method for the manufacture of an electrical bushing for use in a housing of an active implantable medical device,
   whereby the electrical bushing comprises at least one electrically insulating base body and at least one electrical conducting element;
   whereby the conducting element is set-up to establish, through the base body, at least one electrically conductive connection between an internal space of the housing and an external space;
   whereby the conducting element is hermetically sealed with respect to the base body;
   whereby the at least one conducting element comprises at least one cermet;
   characterized in that the method comprises:
      forming a base body green compact having a through-opening that extends through the base body green compact from a ceramic slurry or a ceramic powder;
      generating at least one conducting element green compact from a cermet slurry or a cermet powder;
      producing a bushing blank by combining the at least one conducting element green compact and the base body green compact; and
   separating the bushing blank into at least two electrical bushings;
   characterized in that the ceramic slurry or the ceramic powder is pressed through a first nozzle in order to form the base body green compact, and the cermet slurry or the cermet powder is pressed through a second nozzle in order to form the at least one conducting element green compact.

3. The method according to claim 2, characterized in that the bushing blank is sintered after the step of producing.

4. The method according to claim 2, characterized in that the at least two electrical bushings are sintered after the step of separating.

5. The method according to claim 2, characterized in that the step of forming, producing or generating proceeds in the scope of at least one of the following procedures: uniaxial pressing, cold isostatic pressing, hot isostatic pressing, injection molding or an extrusion procedure.

6. The method according to claim 2, characterized in that the base body and the at least one conducting element comprise a firmly bonded sintered connection, in that the sintered connection is hermetically sealed with respect to gases and liquids.

7. The method according to claim 2, characterized in that the separating includes a disaggregating or a cutting or a chipping with a geometrically defined or undefined cutting form, or a stripping.

8. The method according to claim 2, characterized in that, after completion of the sintering, at least one surface of the electrical bushing is polished and contacted to a metallic pin or wire at least one site of the surface at which a conducting element is arranged.

9. The method according to claim 2 further comprising:
   introducing a filter element in order to change a signal conducted by the at least one conducting element as a function of its frequency and/or amplitude and/or phase.

\* \* \* \* \*